(12) United States Patent
Peczkis et al.

(10) Patent No.: US 6,421,415 B1
(45) Date of Patent: Jul. 16, 2002

(54) ON-LINE SYSTEM FOR QUANTITATIVE ANALYSIS OF MULTI-COMPONENT ADDITIVES AND COATINGS IN SHEET MATERIAL

(75) Inventors: Marek Peczkis, Richmond Hill; Mahendra Munidasa, Thornhill; Piotr Wasowski, Etobicoke, all of (CA)

(73) Assignee: Metso Paper Automation Oy (FI)

( * ) Notice: Subject to any disclaimer, the term of this patent is extended or adjusted under 35 U.S.C. 154(b) by 0 days.

(21) Appl. No.: 09/546,109

(22) Filed: Apr. 10, 2000

Related U.S. Application Data
(60) Provisional application No. 60/135,211, filed on May 21, 1999.

(51) Int. Cl.⁷ .................................. G01T 1/36
(52) U.S. Cl. ........................ 378/46; 378/45; 378/53
(58) Field of Search ................ 378/46, 53, 45

(56) References Cited

U.S. PATENT DOCUMENTS

| | | | | |
|---|---|---|---|---|
| 3,794,843 A | * | 2/1974 | Chen ................ | 250/359.1 |
| 3,868,510 A | * | 2/1975 | Murata et al. ........ | 250/366 |
| 4,081,676 A | | 3/1978 | Buchnea | |
| RE30,884 E | * | 3/1982 | Buchnea ............ | 378/46 |
| 4,815,116 A | * | 3/1989 | Cho ................ | 378/53 |
| 5,854,821 A | | 12/1998 | Chase et al. .......... | 378/53 |
| 5,920,070 A | * | 7/1999 | Petrick et al. ........ | 250/370.09 |
| 6,130,931 A | * | 10/2000 | Laurila et al. ........ | 378/45 |
| 6,157,699 A | * | 12/2000 | Dunn .............. | 378/58 |

FOREIGN PATENT DOCUMENTS

GB      1 565 429      10/1977

* cited by examiner

*Primary Examiner*—Robert H. Kim
*Assistant Examiner*—Chin-Cheng Glen Kao
(74) *Attorney, Agent, or Firm*—Fulwider Patton Lee & Utecht, LLP

(57) ABSTRACT

The present invention is a method and apparatus for calculating the amount and composition of inorganic material in a sheet material. The apparatus of the present invention is capable of calculating the composition of all the additives at once without requiring multiple cycles. The apparatus uses a combination of two techniques, namely an X-ray fluorescence analysis and a preferential X-ray absorption analysis. X-ray fluorescence is measured by a thermoelectrically cooled solid state detector. The apparatus can measure more than three additives. Measurement of argon in the air is used for compensation of electronic drift. An empirical correction is used to compensate for mutual interaction between X-ray fluorescence radiation and clay or talc. The measurement is compensated for dust accumulation by fluorescing the dust.

12 Claims, 12 Drawing Sheets y: bs or Ar

ON-LINE SYSTEM FOR QUANTITATIVE ANALYSIS OF MULTI-COMPONENT ADDITIVES AND COATINGS IN SHEET MATERIAL

This application claims priority of provisional application No. 60/135,211, filed May 21, 1999. That application is incorporated herein by reference.

FIELD OF THE INVENTION

The present invention relates in general to a system for measuring the amount of inorganic material in sheet material such as paper, board, metal, and plastic. More particularly, the invention relates to a method and system for measuring the amount of inorganic material and its composition in sheet, on-line on a production machine, including the measurement of additives in sheet coating.

BACKGROUND OF THE INVENTION

In the paper industry, there is an increasing demand for systems that measure the amount of inorganic material (ash) in paper. There is also a need for high precision calculation of the composition of ash, which entails the measurement of all additives, such as clay, titanium dioxide, etc. in paper. Prior art ash sensors which are based solely on the preferential absorption of X-rays cannot measure the composition of ash since they are not able to measure the presence of each additive separately. Additionally, the sensors can only sufficiently measure total ash when there are no more than minor variations in the composition of ash. There exist gauges that partially compensate for variation in additive composition (e.g. Honeywell-Measurex U.S. Pat. No. 5,854,821). These gauges are capable only of measuring total ash, in presence of up to 3 components, but not each component separately.

One prior art ash sensor is described in U.S. Pat. No. Re 30,884 (a re-issue of U.S. Pat. No. 4,081,676) to Buchnea, entitled "On-line System for Monitoring Sheet Material Additives". The system of Buchnea uses a proportional counter to detect fluorescent X-rays and two separate electronic channels are used to count Ca and Ti X-ray photons, respectively. However, this prior art sensor has the disadvantages of poor energy resolution, extreme sensitivity of its electronic components to temperature and excessively large size. The techniques set forth in Buchnea also suffers from uncertainties in the fluorescent count. In an alternative embodiment, Buchnea contemplates the use of dedicated solid state detectors for each additive, resulting in additional cost and complexity to the system.

It is an object of an aspect of the present invention to provide a new sensor for ash composition measurement which obviates the problems in the prior art.

SUMMARY OF THE INVENTION

The present invention incorporates a novel solid-state sensor and software designed to measure the amount and composition of inorganic material in a sheet material. The sensor is based on nuclear techniques and is capable of measuring the amount of additives such as clay ($Al_2O_3.2SiO_2.2H_2O$), titanium dioxide ($TiO_2$) and calcium carbonate ($CaCO_3$), typical for the paper industry. Other compounds containing either calcium or titanium may also be measured. The system of the present invention may be preferentially used to measure compounds containing elements with fluorescent energies that fall between 5.9 keV and 2.9 keV.

The measurements made by the sensor of the present invention are based on a combination of two techniques. X-ray fluorescence analysis reveals the presence of higher atomic number materials such as calcium or titanium compounds while measurements made by the preferential absorption of X-rays allows lower atomic number materials such as clay, to be measured.

One advantage of the present invention is superior resolution of the fluorescence spectrum obtained thereby, relative to prior art approaches, which allows for simultaneous measurement of multiple additives. Also, temperature stability is achieved using two stage thermoelectric cooling. The size and complexity of the solid-state sensor of the present invention is reduced considerably relative to the prior art. Another advantage is that any small drift in the fluorescence spectrum is compensated for in the system of the present invention by the measurement of argon fluorescence radiation in air and a source backscatter peak of 5.9 keV X-rays. Detection of argon fluorescence peak is only possible due to superior sensitivity of the novel detector of the present invention.

Additional advantages of the detection method according to the present invention include generation of a total additive cross-directional profile with compensation for changes in additive composition; compensation for on-line dust by fluorescing the dust on the window of the detector; and compensation for mutual interaction between X-ray fluorescence radiation generated by higher atomic number additives and clay or talc.

GENERAL DESCRIPTION OF THE FIGURES

An embodiment of the present invention is described below with references to the accompanying drawings, in which.

Figure 3A:
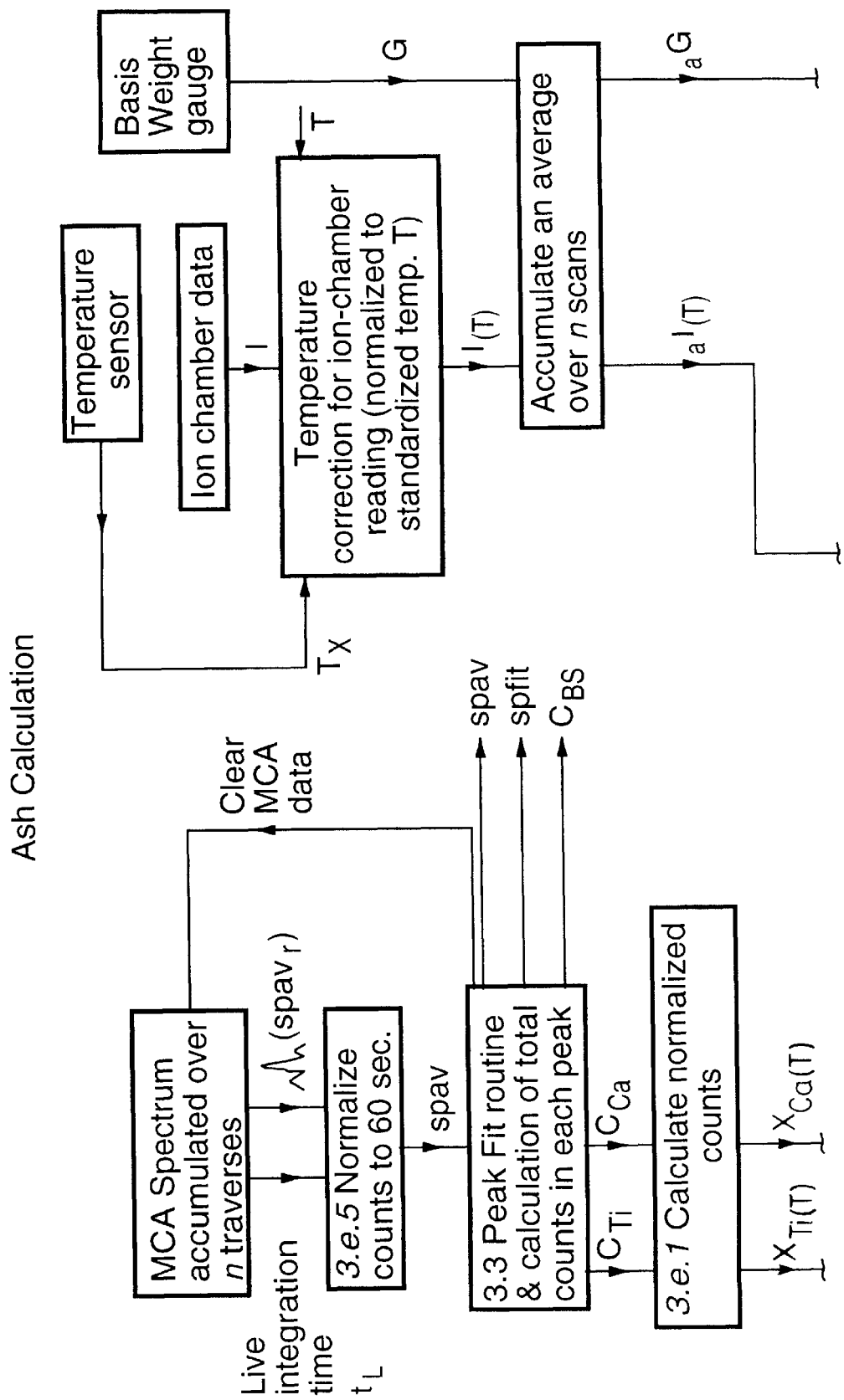
Figure 3B:
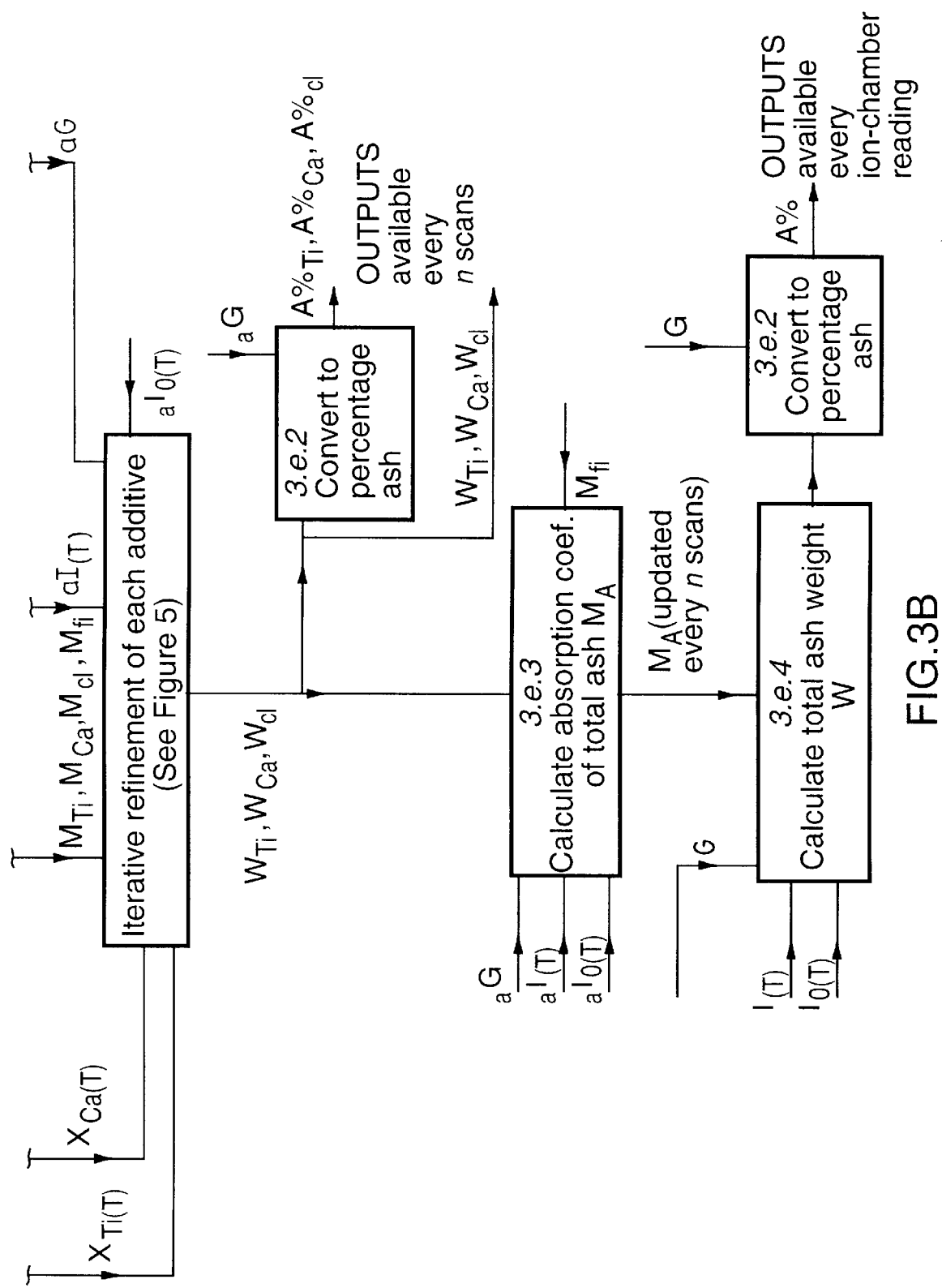
Figure 4:
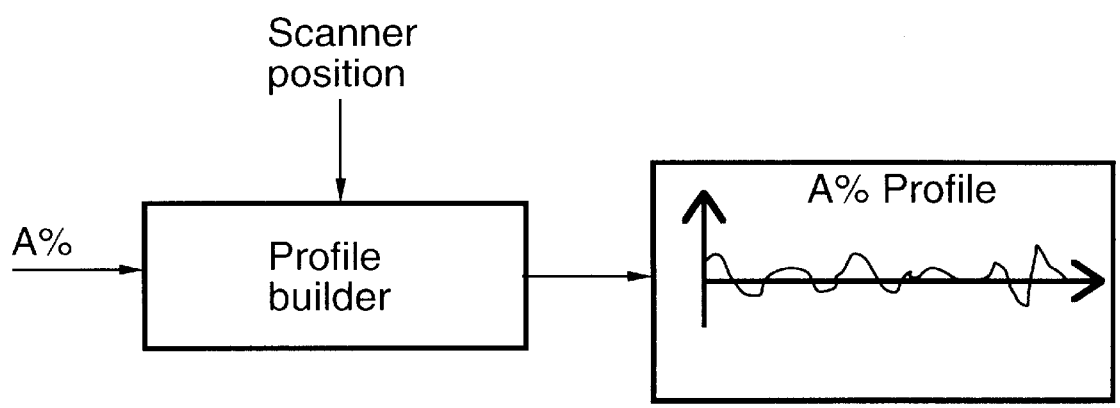
Figure 5A:
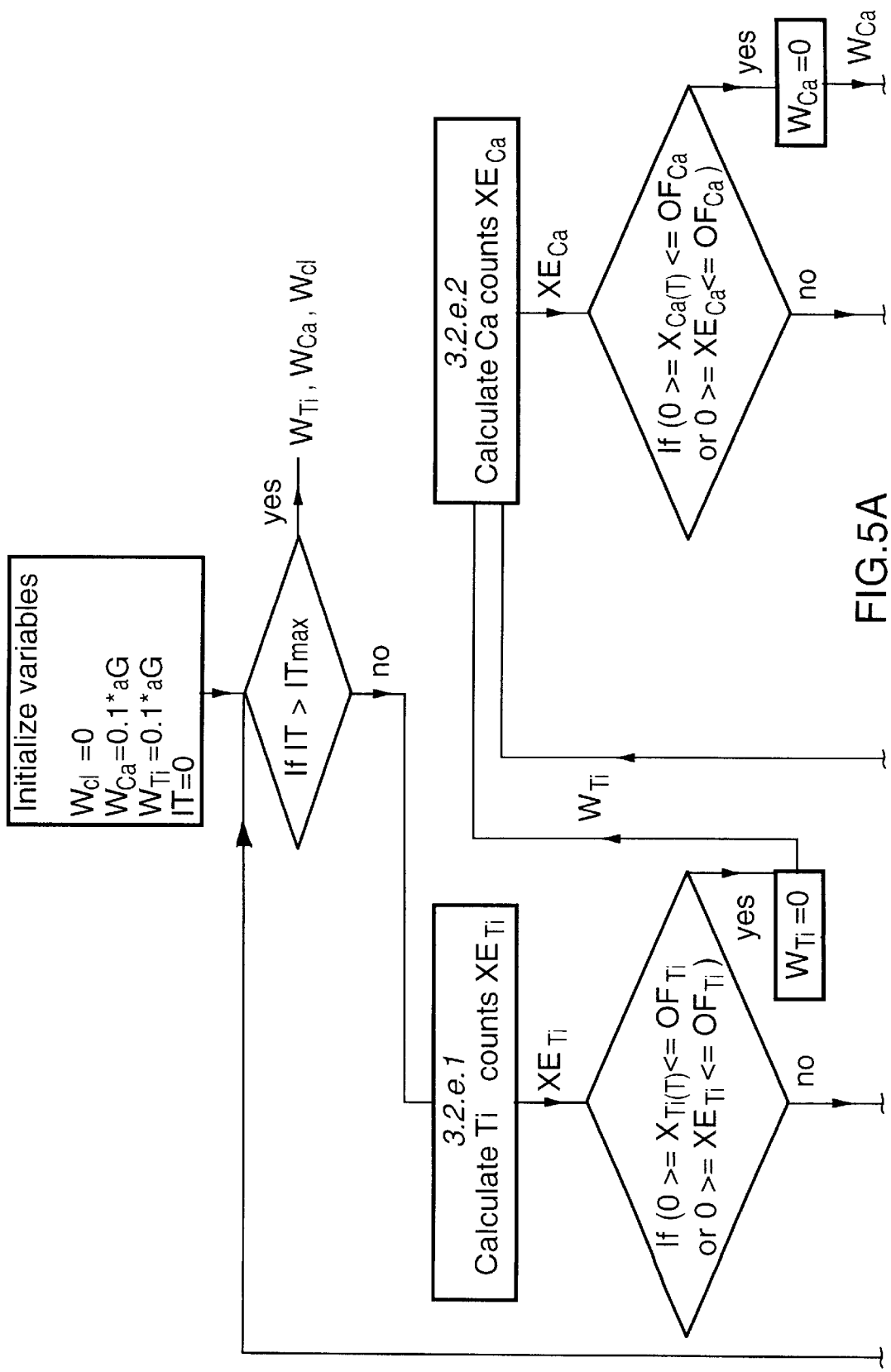
Figure 5B:
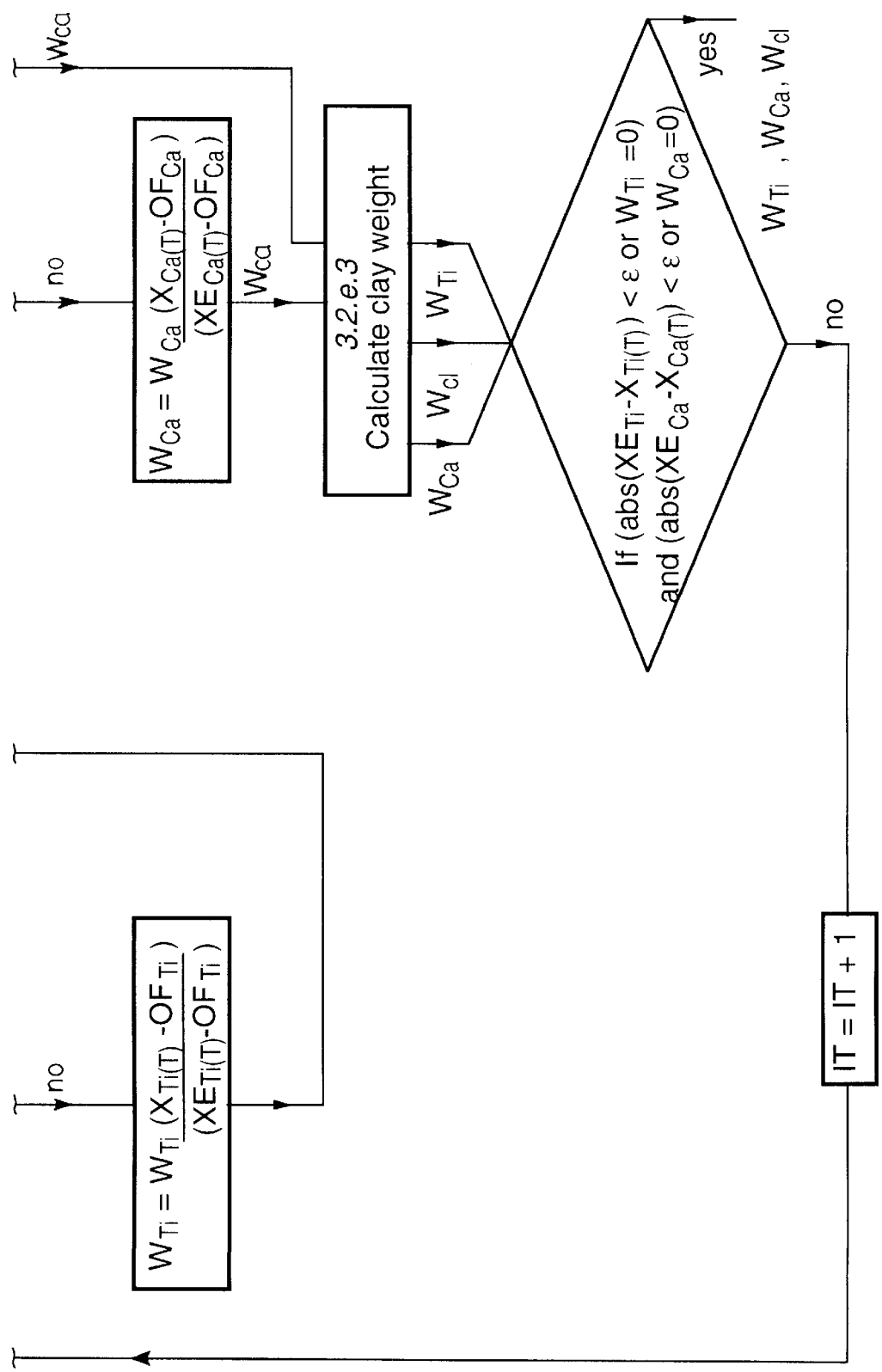
Figure 6:
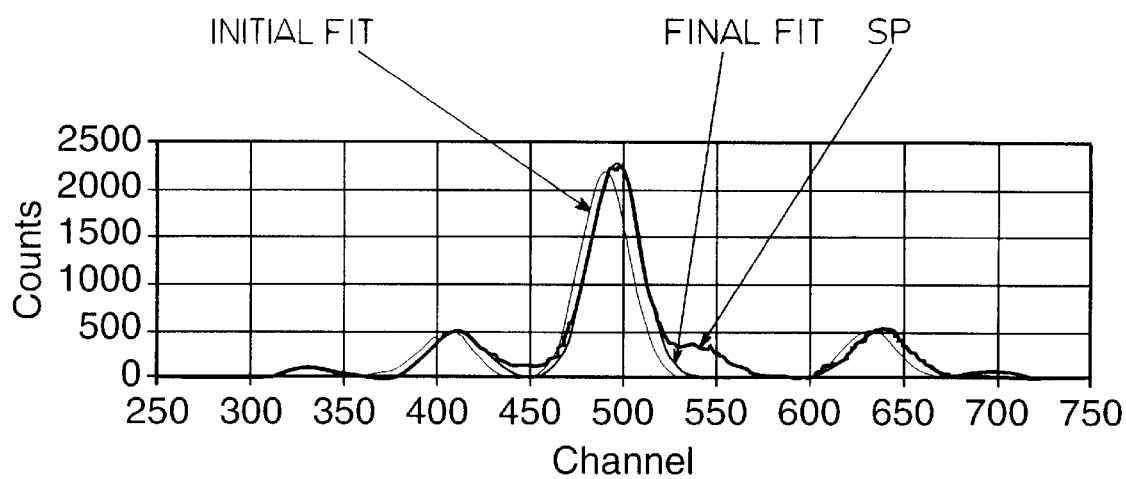
Figure 7A:
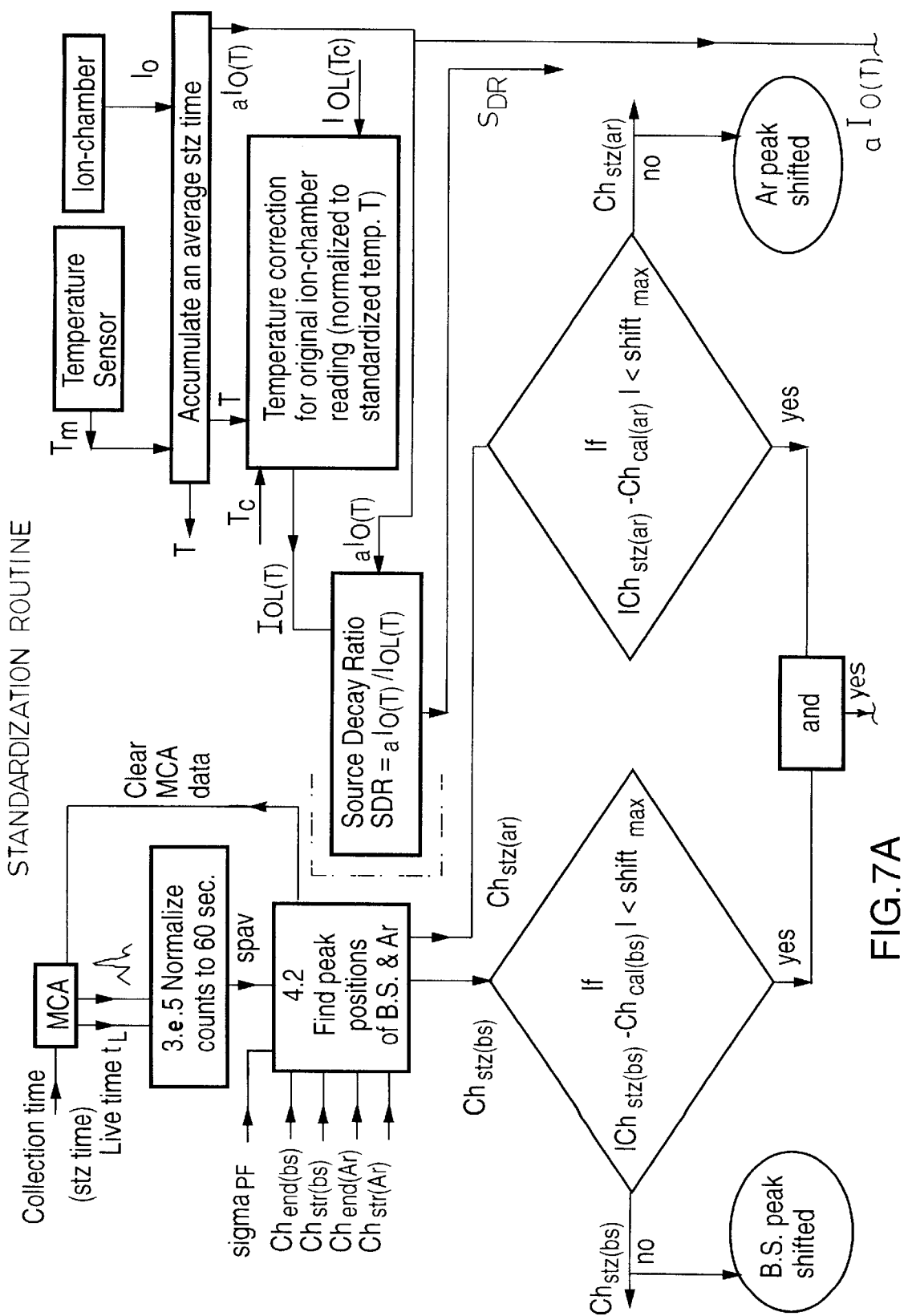
Figure 7B:
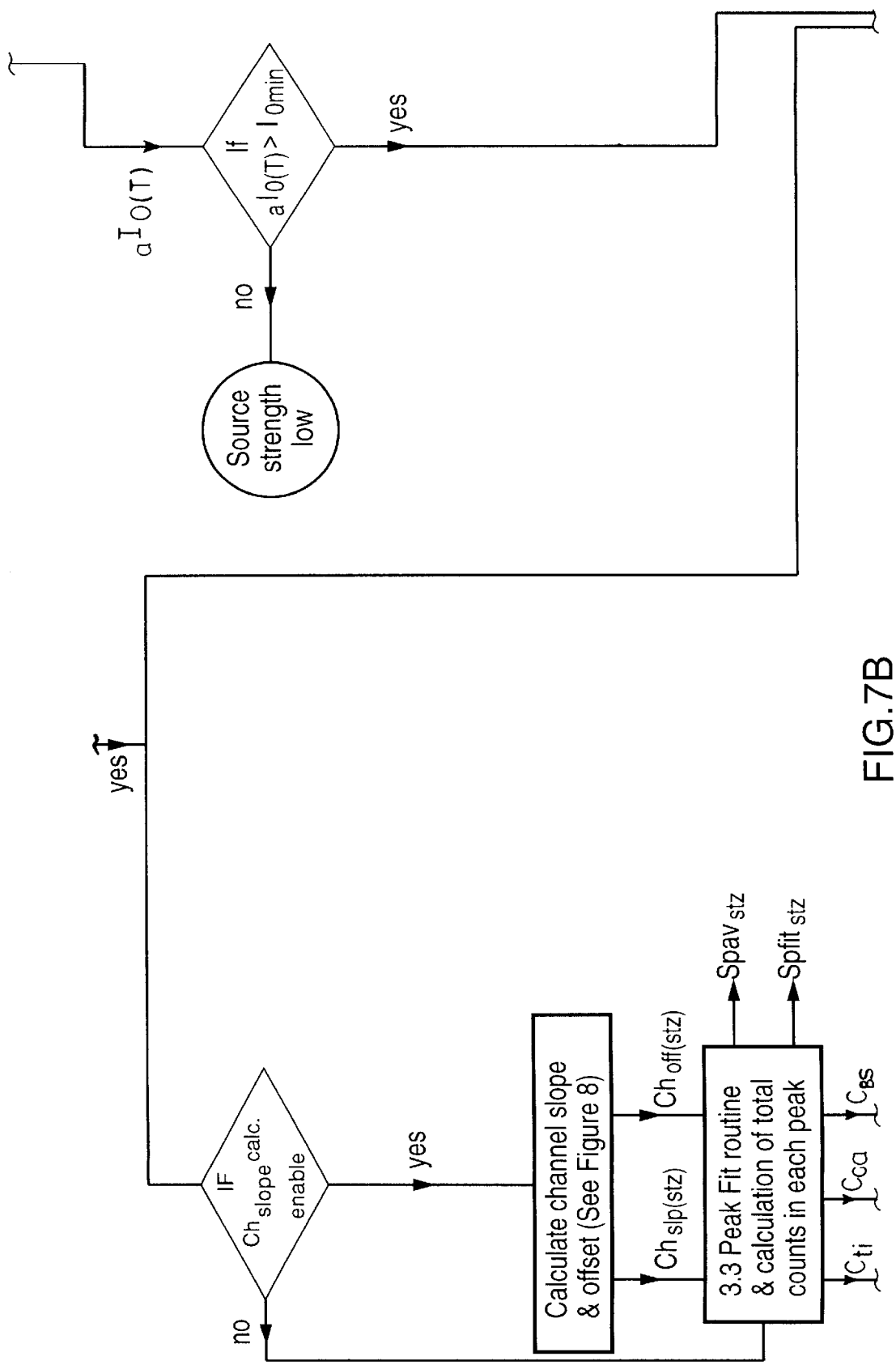
Figure 7C:
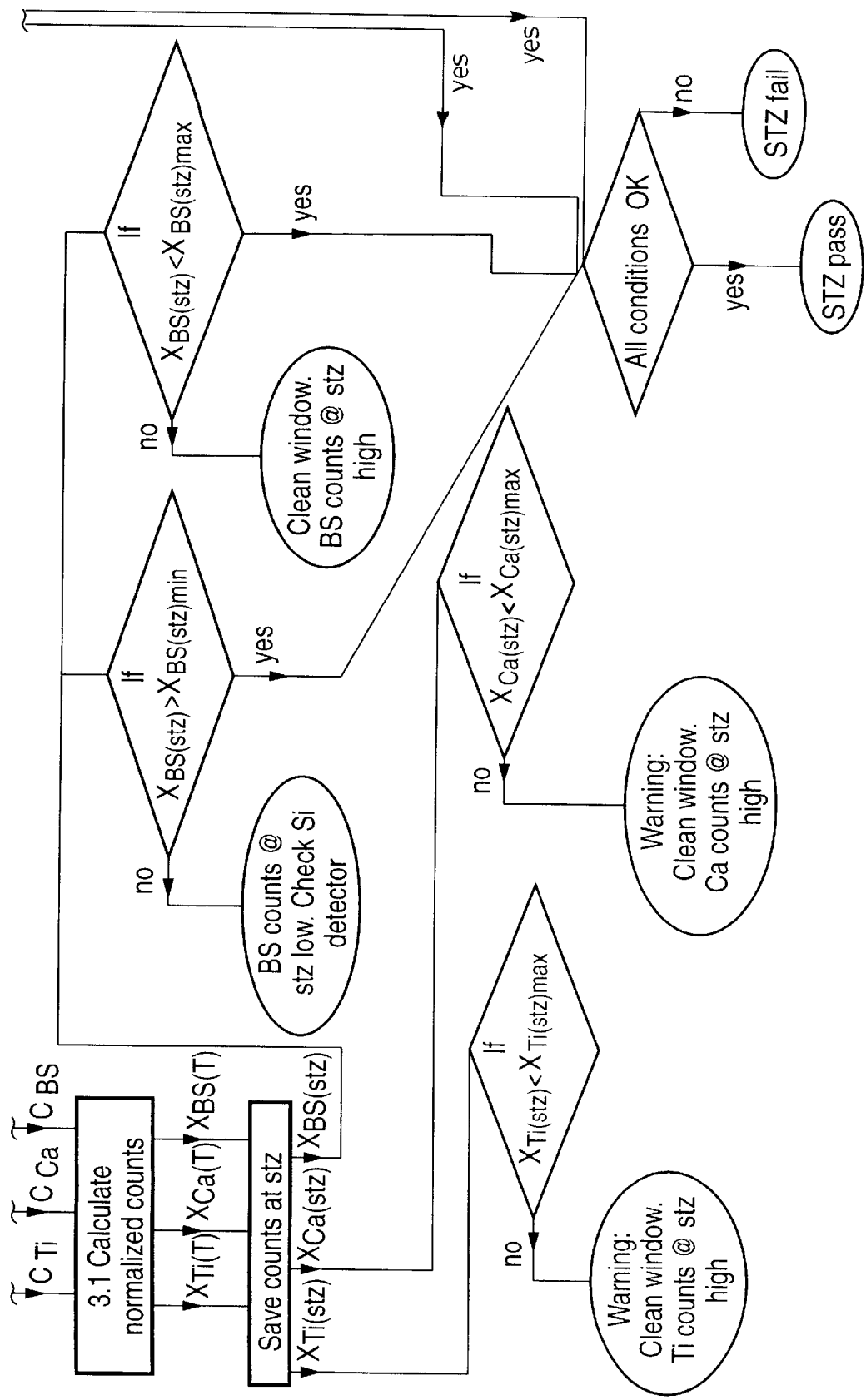
Figure 8:
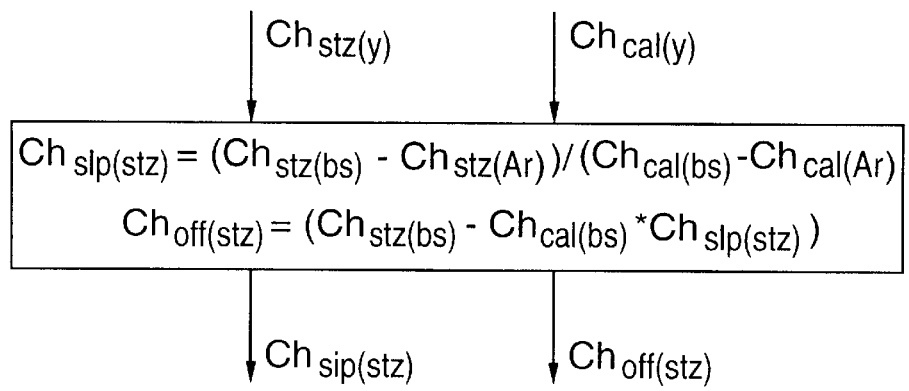
Figure 9:
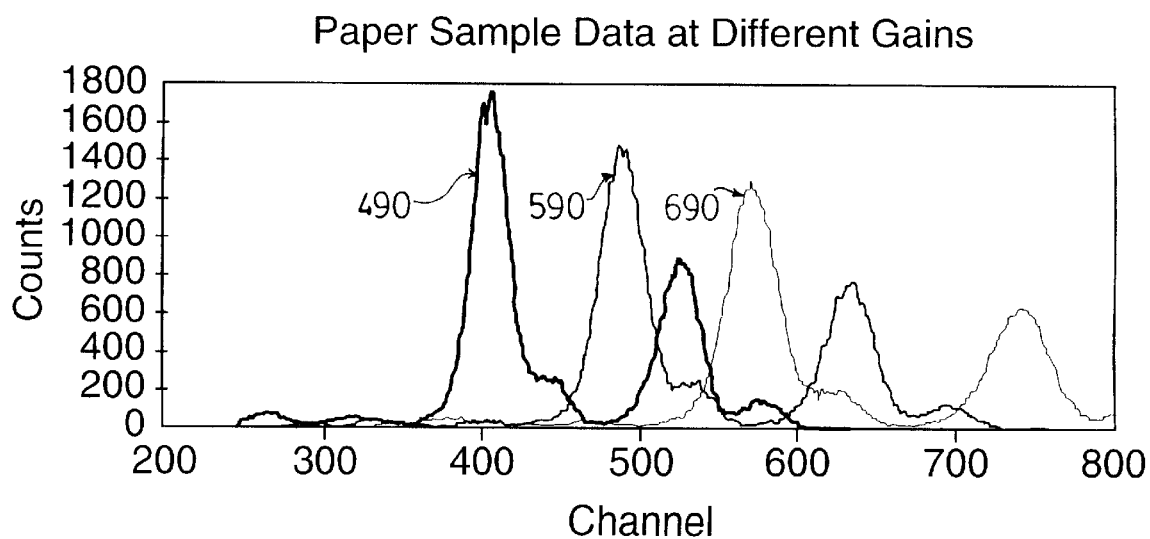

FIG. 3 comprises FIGS. 3A and 3B, and is a flow chart showing steps in a method of calculating total percent ash for constituents, according to the preferred embodiment;

FIG. 4 is a block diagram showing a system for generating a cross-directional profile of total ash weight or percentage across a sheet material, in accordance with an aspect of the invention;

FIG. 5 comprises FIGS. 5A and 5B, and is a flow chart showing the steps iterative refinement of each additive in the method of FIG. 3;

FIG. 6 is a graph showing raw spectrum, initial fit and final spectrum resulting from the fitting algorithm;

FIG. 7 comprises FIGS. 7A, 7B and 7C, and is a flow chart showing steps in a standardization routine according to the preferred embodiment;

FIG. 8 is a flow chart showing details of the step of calculating channel slope and offset for the method of FIG. 7B; and FIG. 9 is a graph showing paper sample data at different spectroscopy amplifier gain levels.

DETAILED DESCRIPTION OF THE PREFERRED EMBODIMENTS

The present invention provides an improved method and system for on-line measurement of the amount of inorganic material, and its composition, in a sheet material. This is preferably achieved on a paper machine. It will be understood that the composition of any sheet material other than paper may be calculated using the method and system of the present invention.

The composition of paper generally involves the use of inorganic material. The composition of the inorganic material is known by those skilled in the art as "additives" or ash. Examples of additives include clay, Titanium Dioxide and Calcium Carbonate.

Figure 1:
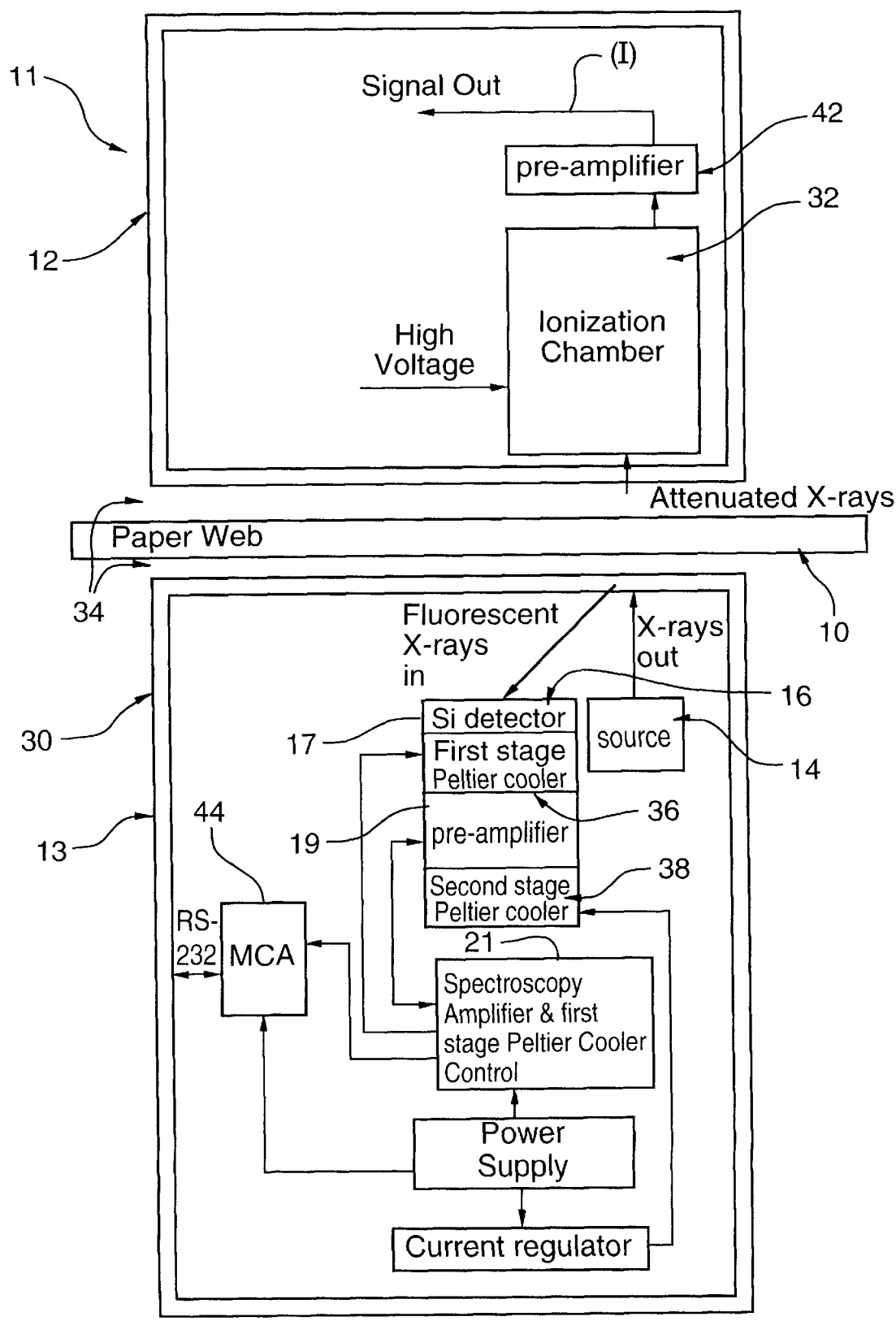
FIG. 1 is a schematic view of a sensor according to a preferred embodiment of the present invention.

Turning to FIG. 1, an ash sensor 11 is shown according to the present invention. In operation, a paper web 10 passes through the ash sensor 11. The sensor 11 comprises an absorption detector unit 12 (occasionally referred to herein as the Detector Head, (DH)), a radiation source 14 and a fluorescence detector unit 16, both of which are housed within a Source Head (SH) identified by reference numeral 13. X-rays emitted by the radiation source 14 irradiate the paper web 10 as it passes between the DH 12 and SH 13, separated by a minimum free air gap 34. It will be understood that the term "X-ray" as used in this disclosure also includes gamma rays. Some of the X-rays, known as exit X-rays, are attenuated by the paper web 10 before reaching the absorption detection unit 12. The absorption detection unit 12 collects the exit X-rays and provides a signal (I) based on the intensity of the exit X-rays collected. The intensity signal is transmitted to a computing means, as shown and described in greater detail below with reference to FIG. 3. Some X-rays, known as fluorescent X-rays, are emitted by the paper web 10 back towards the fluorescence detector unit 16. The fluorescence detector unit 16 collects the fluorescent X-rays and provides signals based on the intensity and energy of the collected X-ray signals to the computing means. The computing means, in turn, calculates the amount of inorganic material, and its composition, in the paper web 10 based on the signals provided by the absorption detector unit 12 and the fluorescence detector unit 16, as discussed in greater detail below with reference to FIG. 3.

Both the absorption detector unit (DH 12) and the SH 13 are constructed using insulated double walls 30 surrounding respective air chambers supplied with dry air, and which are water cooled. The DH 12 encloses a detector 32 in the form of an ionization chamber and a pre-amplifier 42. The ionization chamber is connected to a high-voltage supply and functions as a charge integrating device with current flow (I) directly related to the total amount of radiation entering the chamber. The current measurements are then sent from the pre-amplifier 42 to the computing means of FIG. 3 for calculation of the content of inorganic material in the paper.

The radiation source 14 directs X-ray radiation onto the web 10 from the same side as the fluorescence detector unit 16. The radiation source 14 is preferably a 100 mCi soft X-ray radioactive source such as $^{55}$Fe. It will be known by those skilled in the art that $^{55}$Fe is an isotope which decays to $^{55}$Mn through pure electron capture and therefore, most of the resulting X-ray photons due to the re-arrangement of the atomic structure of $^{55}$Mn after the electron capture process, have an energy at 5.9 keV. The $^{55}$Fe isotope emits low energy X-rays. As discussed above, the ionization chamber of the absorption detector unit 12 monitors the intensity of the radiation from the source 14 which is transmitted through the paper web 10. The fluorescence detector unit 16 detects the fluorescent X-rays which result from excitation of the ash constituents within the web 10.

The fluorescence detector unit 16 preferably comprises a solid state X-ray detector 17 with a silicon-PIN photodiode, a charge sensitive pre-amplifier 19, a spectroscopy grade shaping amplifier 21 connected to a power supply which in turn is connected to a current regulator, and a multichannel analyzer (MCA) 44 with an RS-232 port.

Use of the solid state X-ray detector, as opposed to a proportional gas counter (as in the prior art), generates a larger charge per unit energy when the fluorescence X-rays interact with silicon atoms in the photodiode. When the fluorescence X-rays interact with the silicon atoms, an average of one electron/hole pair is created for every 3.62 eV of energy lost in the atom. Ionization of a gas requires approximately 30 eV per ion pair. The solid-state detector is then thermo-electrically cooled to approximately −30° by means of a first stage Peltier cooler 36 and second stage Peltier cooler 38. This detector provides more accurate measurements of the intensity and energy of the fluorescence X-rays than is provided for in the prior art.

Figure 2:
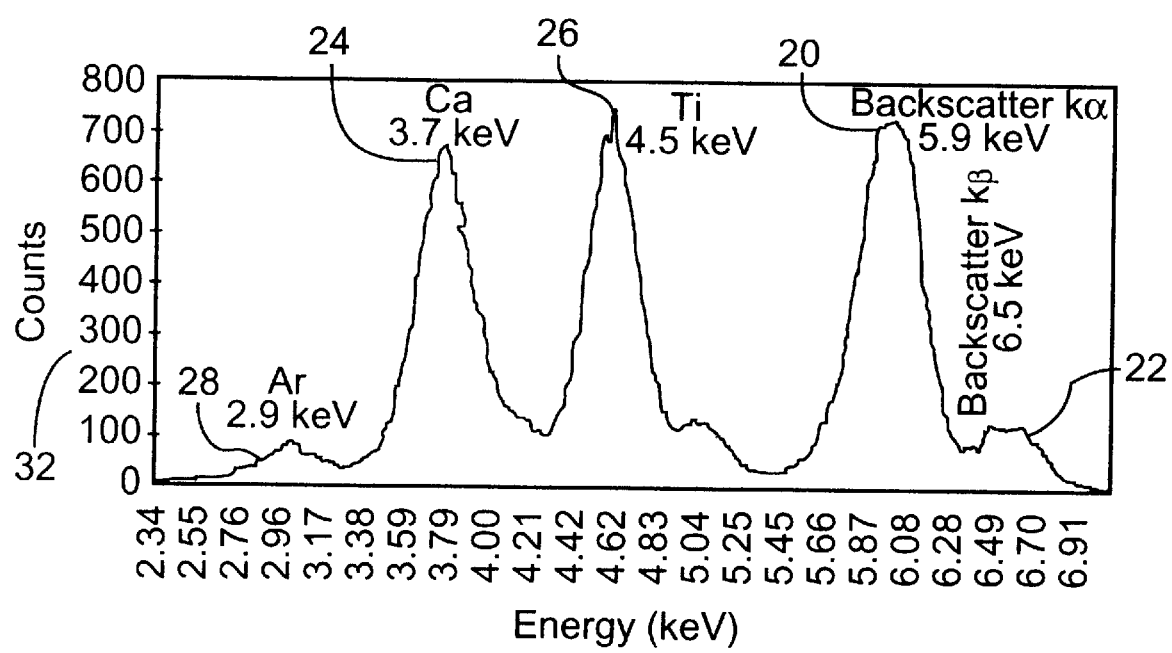
FIG. 2 is a sample X-ray fluorescent spectrum produced by the sensor of the present invention.

A sample X-ray fluorescence spectrum generated by the fluorescence detection unit 16 is shown in FIG. 2. Due to the large number of electron/hole pairs produced in the fluorescence detector unit 16, enough charge gain is produced to allow a measurable charge pulse for each X-ray photon. Since the resulting pulse height is proportional to the energy of the X-ray photon which produced it, the solid state detector, together with the MCA 44 produces a fluorescent X-ray energy spectrum which is capable of a resolution as high as 200 eV. The high resolution X-ray spectrum allows all additives in the paper web to be measured at once (as seen by the multiple peaks).

As discussed above, the measurements made by the sensor to calculate the composition of all the inorganic material additives in the paper web are based on a combination of two techniques: X-ray fluorescence analysis and the preferential absorption of X-rays. X-ray fluorescence analysis reveals the presence of higher atomic numbered materials such as calcium or titanium compounds while the preferential absorption of exit X-rays measures the lower atomic number materials such clay. The signals provided by the absorption detector unit 12 and the fluorescence detector unit 16 are used for this calculation.

A more detailed description of the calculation of the amount and composition of inorganic material in paper is now provided. The preferential absorption technique is utilized in relation to the measurements and signal provided by the absorption detector unit 12. This technique refers to the varying absorption effect of components in the paper web 10 on an X-ray which is passed through the web 10. This technique requires the interaction of the radiation source 14, the paper web 10 and the absorption detector unit 12. As shown in FIG. 1, the source 14 is placed on one side of the paper web 10 and radiation transmitted through the paper web 10 is measured by the absorption detection unit 12 which is located opposite the radiation source. The intensity of the exit X-rays entering the absorption detector unit 12 may be expressed as:

$$I=I_o \exp(-MG) \tag{1}$$

where $I_o$ is the measured radiation intensity with no paper web present;

I is the measured radiation intensity with the paper web present;

G is the basis weight of the paper (mass per unit area); and

M is the average mass absorption coefficient of the paper web for the particular energy of radiation being used (area per unit mass).

If the paper consists of two components, cellulose and a single additive, M can be written as:

$$M = AM_1 + (1-A)M_2 \qquad (2)$$

where A is the fraction of the additive in the paper mass;

$M_1$ is the mass absorption coefficient of the additive for the particular energy of radiation being used; and $M_2$ is the mass absorption coefficient of cellulose for the particular energy of radiation being used.

The basis weight, G, of the paper web is known through use of a basis weight gauge (FIG. 3A), as is well known in the art, or a pre-set value can be stored in a register, instead, such that Equation 2 may be substituted into Equation 1 to produce an equation to yield concentration of the additive:

$$A = [(1/G)\ln(I_o/I) - M_2]/(M_1 - M_2) \qquad (3)$$

or the additive weight per unit area, W:

$$W = [\ln(I_o/I) - GM_2]/(M_1 - M_2) \qquad (4)$$

It will be understood from a review of Equations 3 and 4 that this technique may only be used if the absorption coefficients of clay and cellulose are different. It will be understood by one skilled in the art that the sensitivity of the measurement of the additive increases as $M_1$ becomes larger relative to $M_2$, hence the term preferential absorption.

It will also be understood by one skilled in that art that problems may arise if more than one type of ash is present in the paper web 10. The preferential absorption technique is unable to provide individual concentrations of each of the ash constituents, or additives. Since the mass absorption coefficients of each of the paper additives are different, the total ash measurement is correct only when the paper consists of one ash constituent or the composition is constant. Therefore, the X-ray fluorescence technique is implemented according to the present invention, in order to calculate the content of all the additives in the paper web 10. The energy of the fluorescent X-rays is unique to each element.

Returning to FIG. 2, the peaks, 20 and 22, corresponding to 5.9 keV and 6.5 keV, respectively, are direct back scattered measurements of X-rays emitted by the radiation source 14 and the 3.7 keV 24 and 4.5 keV 26 peaks correspond to Ca and Ti respectively. The 2.9 keV peak 28 is generated by the fluorescence created by argon atoms in the free air gap 40 separating the web 10 and Source Head 13. The counts on the y-axis 32 represent the number of pulses, or counts, of the corresponding additive or backscatter measurement. The secondary peaks to the right of the major peaks are due to lower probability transitions. Thus, the energy of the X-ray radiation signifies the presence of a particular element, and the intensity of the radiation is a measure of its concentration. The X-ray spectrum may also be used to correct the preferential absorption measurement of clay. In order to calculate the amount and composition of the inorganic material, the measurements of intensity and energy of the fluorescence X-rays are required.

A sample calculation is now provided to more clearly illustrate the X-ray fluorescence analysis and preferential absorption of X-ray techniques discussed above. The specific calculation, with compensation for external influences, is performed by the computing means discussed in greater detail below with reference to FIG. 3.

For the sample calculation, it is assumed that the paper web 10 contains the additives, $CaCO_3$, $TiO_2$ and clay. The attenuated X-ray intensity detected by the ionization chamber is given by the equation:

$$I = I_o \exp(-M_{5.9} G) \qquad (5)$$

where $M_{5.9}$ is the average mass absorption coefficient of the paper web. $M_{5.9}$ can be calculated using the following equation.

$$M_{5.9} = A_{Ti}M_{Ti(5.9)} + A_{Ca}M_{Ca(5.9)} + A_{cl}M_{cl(5.9)} + (1 - A_{Ti} - A_{Ca} - A_{cl})M_{fi(5.9)} \qquad (6)$$

or $$M_{5.9} = [W_{Ti}M_{Ti(5.9)} + W_{Ca}M_{Ca(5.9)} + W_{cl}M_{cl(5.9)} + (G - W_{Ti} - W_{Ca} - W_{cl})M_{fi(5.9)}]/G \qquad (7)$$

where $A_y$ is the fraction of constituent y in the paper mass;

$W_y$ is the weight per unit area of constituent y in the paper mass; and $M_{y(x)}$ is the mass absorption coefficient of constituent y for the particular energy x of radiation being used.

It will be understood that "Ca" represents Calcium, "cl" represent clay, "Ti" represent titanium and "fi" represents fibre.

In actual fact, Equation 5 is preferably calculated with the mass absorption coefficients ($M_{y(5.9)}$ and $M_{y(6.5)}$) corresponding to the 5.9 keV and 6.5 keV values. It will be understood that any error introduced by using only the majority X-ray energy (5.9 keV) is compensated in the calibration procedure described below.

Taking the natural logarithm of equations 5 and 7 combined, the weight of the clay, $W_{cl}$, can be calculated as follows:

$$W_{cl} = \frac{[\ln(I_0/I) - W_{Ti}(M_{Ti(5.9)} - M_{fi(5.9)}) - W_{Ca}(M_{Ca(5.9)} - M_{fi(5.9)}) - GM_{fi(5.9)}]}{(M_{cl(5.9)} - M_{fi(5.9)})} \qquad (8)$$

It will be understood that similar calculations may be made to calculate the weight of the other additives. However, it is clear that the weight of only one of the additives may be ascertained. The relationship between the intensity of the fluorescent X-rays and the additive concentrations are described by the equation shown below. Assuming that the penetration of the radiation into the paper web 10 is small compared with the distance between the radiation source 14 and the paper web 10 and the distance between the paper web 10 and fluorescent detector unit 16, it will be understood that the fluorescent X-ray intensity, $X_y$, of energy r generated by the constituent y, measured by the solid state detector is:

$$X_y = \{K_y W_y[1 - \exp[-(E_{tr}M_{5.9} + E_{fl}M_r)G]]\}/\{G(E_{tr}M_{5.9} + E_{fl}M_r)\} \qquad (9)$$

where $M_r$ is the average mass absorption coefficient of the paper for the fluorescent X-ray energy r generated by the constituent y;

$E_{tr}$ is a geometrical factor which depends on the angle of incidence of the 5.9 keV radiation (equal to unity for normal incidence);

$E_{fl}$ is a geometrical factor which depends on the angle of emission of the fluorescent radiation (equal to unity for emission normal to the paper).

$$M_{(r)} = [W_{Ti}M_{Ti(r)} + W_{Ca}M_{Ca(r)} + W_{cl}M_{cl(r)} + (G - W_{Ti} - W_{Ca} - W_{cl})M_{fi(r)}]/G \qquad (10)$$

where $M_{y(r)}$ is the mass absorption coefficient of individual constituents y for fluorescent X-ray energy r.

The factor $K_y$ is a combination of a geometrical constant, a detector efficiency, an absorption factor in the beryllium window, a source emission intensity, a fluorescence yield for the X-ray transition excited and a photoelectric cross section for that transition. With respect to the present invention, two assumptions may be made. Firstly, the normal incidence assumption ($E_{tr}=E_{fl}=1$) is a good approximation for the broad beam geometry used in the present invention and secondly, the assumption of low penetration is good at all energies for thin specimens such as paper.

Therefore, the 4.5 keV fluorescent X-ray intensity due to $TiO_2$ is given by:

$$X_{Ti}=\{K_{Ti}W_{Ti}[1-\exp[-(E_{tr}M_{5.9}+E_{fl}M_{4.5})G]]\}/\{G(E_{tr}M_{5.9}+E_{fl}M_{4.5})\} \quad (11)$$

where $$M_{4.5}=[W_{Ti}M_{Ti(4.5)}+W_{Ca}M_{Ca(4.5)}+W_{cl}M_{cl(4.5)}+(G-W_{Ti}-W_{Ca}-W_{cl})M_{fi(4.5)}]/G \quad (12)$$

Similarly, the 3.7 keV fluorescent X-ray intensity due to $CaCO_3$ is defined by $$X_{Ca}=\{K_{Ca}W_{Ca}[1-\exp[-(E_{tr}M_{5.9}+E_{fl}M_{3.7})G]]\}/\{G(E_{tr}M_{5.9}+E_{fl}M_{3.7})\} \quad (13)$$

where $$M_{3.7}=[W_{Ti}M_{Ti(3.7)}+W_{Ca}M_{Ca(3.7)}+W_{cl}M_{cl(3.7)}+(G-W_{Ti}-W_{Ca}-W_{cl})M_{fi(3.7)}]/G \quad (14)$$

It can be seen from the above equations that the individual measurements of the additives are interrelated. This is due to the fact that the fluorescent radiation is also absorbed by all the measured components. Also, the clay measurement based upon the ionization chamber signal depends upon the amount of other additives.

Equations 7, 8, 11, 12, 13 and 14 are solved simultaneously to calculate the individual ash component weights, $W_y$, through an iterative procedure. The initial weights for the iterative solution are 0% for clay and 10% of basis weight for Ca and Ti. The calculations continue until the calculated counts reach the measured counts or when the number of iterations reach a predetermined maximum, whichever occurs first. The constants $K_y$ and $M_{y(r)}$ are determined through a calibration procedure using paper samples with a known amount of a single additive.

It will be understood by those skilled in the art that the fluorescence detector unit 16 must be calibrated in order to ensure accurate measurements. In order to obtain accurate measurements for the constants $K_y$ and $M_{y(r)}$, at least three sets of samples are required. These samples involve: (1) $TiO_2$ and fiber only, at a known basis weight and a varying but known concentration; (2) $CaCO_3$ and fiber only, at a known basis weight and a varying but known concentration; and (3) clay and fiber only, at a known basis weight and a varying but known concentration. For each sample, the intensity measurement from the ionization chamber signal (I) and the signal with no sample present ($I_o$) are measured. For each sample eqs. 5 and 7 can be written as:

$$\ln(I_o/I)=W_y(M_{y(5.9)}-M_{fi(5.9)})+GM_{fi(5.9)} \quad (15)$$

The plot resulting from $\ln(I_o/I)$ vs. $W_y$ provides a slope of ($M_{y(5.9)}-M_{fi(5.9)}$) and a y-intercept of $GM_{fi(5.9)}$ for each sample. Provided that the base weight, G, is known, this graph provides the mass absorption coefficients of each separate additive and fiber at a source X-ray energy of 5.9 keV. The corresponding mass absorption coefficients at fluorescent X-ray energies can be calculated by referring to the values listed in Table 1 and Equations 8, 9, 12 and 14.

TABLE 1

| | Mass Absorption Coefficient | | |
|---|---|---|---|
| Paper Constituents | Exciting Photons 5.9 keV ($M_{y(5.9)}$) | Fluorescent Photons | |
| | | 4.5 keV ($M_{y(4.5)}$) | 3.7 keV ($M_{y(3.7)}$) |
| Fiber | $M_{fi(5.9)}$ | 2.25142 * $M_{fi(5.9)}$ | 4.58731 * $M_{fi(5.9)}$ |
| $TiO_2$ | $M_{Ti(5.9)}$ | 0.32251 * $M_{Ti(5.9)}$ | 0.63197 * $M_{Ti(5.9)}$ |
| $CaCO_3$ | $M_{Ca(5.9)}$ | 2.00000 * $M_{Ca(5.9)}$ | 0.75987 * $M_{Ca(5.9)}$ |
| Clay | $M_{cl(5.9)}$ | 2.14628 * $M_{cl(5.9)}$ | 4.12189 * $M_{cl(5.9)}$ |

The fluorescence signal $X_y$ is obtained for each sample at a fixed integration time of 60 s. In this calculation, each fluorescence peak is fitted to a Gaussian profile and $X_y$ is calculated from the total area under the Gaussian profile. By using eq. 9 and plotting $$X_y \text{ vs. } \{W_y[1-\exp[-(E_{tr}M_{5.9}+E_{fl}M_r)G]]\}/\{G(E_{tr}M_{5.9}+E_{fl}M_r)\}$$

for each sample, a value for $K_y$ may be obtained from the slope of the plot. In practice, an offset $OF_i$ is added to eq. 9 to achieve a better fit. The values of $E_{tr}$ and $E_{fl}$ may initially be set to unity. After all slopes and offsets are calculated, the value for $E_{tr}$ and $E_{fl}$ may be readjusted to minimize the error over all of the samples. After the calibration process, all of the constants in eqs. 7, 8, 11, 12, 13 and 14 are known. The concentration of the individual additives from the paper web 10 with multiple additives can be calculated using the sensor readings. The above equations are known in the prior art.

The inventors' experience has shown that whenever there is clay mixed with another constituent ($TiO_2$ and/or $CaCO_3$), the above-mentioned theoretical formulae known in the prior art do not correctly model the Ti and Ca fluorescent counts measured by the sensor. It has been found that the difference between the measured counts and the calculated counts is related to the clay weight in the sample. Mixed samples with only Ti and Ca agree with the existing formulae. Based upon these observations, the inventors have conceived of an empirical correction to the existing formulae.

Specifically, the empirical correction $(1+\alpha W_{clay})$ can be used to multiply the existing formula (Eq. (9)) to correct fluorescence counts. The factor 1 makes sure that the counts will be unaffected when there is no clay. The factor $\alpha$ is an additional calibration parameter. Therefore, the new formula for counts becomes $$X_y = \frac{(1+\alpha W_{clay})K_y W_y}{G(E_{tr}M_{5.9}+E_{fl}M_r)}\{1-\exp[-(E_{tr}M_{5.9}+E_{fl}M_r)G]\}+OF_y$$

In order to calculate $\alpha$ at calibration, all of the calibration parameters, except $\alpha$, are found in the same way as discussed above, using single component ash samples. The value $\alpha$ has no effect on single component samples. Then, Ti and Ca counts are measured for a few mixed samples with clay. Then, the term $$\frac{K_y W_y}{G(E_{tr}M_{5.9}+E_{fl}M_r)}\{1-\exp[-(E_{tr}M_{5.9}+E_{fl}M_r)G]\}$$

is calculated for each sample for both Ti and Ca. The measured counts are then divided by the corresponding calculated value:

$$X_y^{measured} \bigg/ \frac{K_y W_y}{G(E_{tr}M_{5.9} + E_{fl}M_r)} \{1 - \exp[-(E_{tr}M_{5.9} + E_{fl}M_r)G]\}$$

for both Ti and Ca in each sample. The above term may then be plotted as (Y) vs. Clay weight (X) for Ti and Ca separately. The slope of this plot is $\alpha$. In the event of any small difference between the values obtained from the Ti counts and Ca counts, the average of the two $\alpha$ is used.

Although a fluorescent radiation measurement takes significantly longer than the ionization chamber integration time, total ash weight W can be instantaneously obtained (typically 20 ms) from the ionization chamber reading by re-arranging eq. 4 to:

$$W = [\ln(I_o/I) - GM_{fi}]/(M_A - M_{fi}) \quad (16)$$

where $M_A$ is the average mass absorption coefficient given by the equation $$M_A = [W_{Ti}M_{Ti(5.9)} - W_{Ca}M_{Ca(5.9)} + W_{cl}M_{cl(5.9)}]/(W_{Ti} + W_{Ca} + W_{cl}) \quad (17)$$

$M_A$ may be updated every time the ash constituent weights are available which allows a total ash cross-directional profile to be achieved.

FIG. 3 is a flowchart showing calculation of the total percent ash A% and percent ash for constituents A %$_{Ti}$, A%$_{Ca}$, A%$_{cl}$, according to a preferred embodiment of the present invention.

A description of the terms used in the flowcharts appears in Appendix A to this disclosure. Furthermore, where a box appears in FIG. 3 bearing an identification number (e.g. 3.e.1, 3.e.2, etc.), a reference will be found in Table 2 to an explanatory equation identified by an identical identification number.

The instantaneous value of total percent ash is generated as discussed generally above and, for a gauge traversing across the sheet, can be used to create profiles (FIG. 4). A cross-directional profile, as understood in the context of this specification, is a scan line image across the width of the sheet representative of total ash weight or percentage. The percent compositions A%$_{Ti}$, A%$_{Ca}$, A%$_{cl}$, on the other hand, are available only at longer time intervals that typically correspond to several traverses across the sheet. The absorption coefficient of total ash depends upon the composition and is updated each time the new composition is evaluated. This, however, does not represent a disadvantage because the composition changes much more slowly than the total ash. In addition to percentages, weights of constituents in uncorrected form $W_{Ti}$, $W_{Ca}$, $W_{cl}$ and Slope and Offset corrected forms $W'_{Ti}$, $W'_{Ca}$, $W'_{cl}$ are generated as discussed below.

TABLE 2

3.e.1. Normalized counts to original source activity
$X_{y(O)} = C_y/S_{DR}$
3.e.2. Convert to percentage ash $$A\%y = \frac{W_y}{G} * 100 \text{ for each } y; \ y = Ti, Ca, \text{ or } cl; \ G \text{ is either}$$

instantaneous or accumulated 3.e.3 Calculate absorption coefficient of total ash $M_A$ TABLE 2-continued $$M_A = \frac{\left[\ln\left(\frac{aI_{0(T)}}{aI_{(T)}}\right) - _aGM_{fi}\right]}{W'_{Ti} + W'_{Ca} + W'_{cl}} + M_{fi}$$

3.e.4 Calculate total ash weight W'

$$W' = \frac{\left[\ln\left(\frac{aI_{0(T)}}{I_{(T)}}\right) - GM_{fi}\right]}{(M_A - M_{fi})}$$

3.e.5 Normalize counts to 60 sec.
spav$_r$ = spav * 60/t$_L$

The procedure at step 3.e.1 corrects count rates by factors accounting for radioisotope activity loss and difference in the present temperature and temperature at standardization.

The source decay factor $S_{DR}$ is defined as the ratio of the open-gap ion chamber signals at standardization and at the calibration time.

A temperature sensor measures the air gap temperature. All measurement signals are normalized to temperature at standardization.

The normalized counts and temperature corrected average ion chamber signal from block 3.e.1 are subjected to self-consistence analysis in the iterative refinement procedure set forth in FIG. 5 with reference to Table 3.

TABLE 3

3.2.e.1 Calculate Ti counts XE$_{Ti}$ $$M_{5.9} = \frac{W_{Ti}M_{Ti(5.9)} + W_{Ca}M_{Ca(5.9)} + W_{cl}M_{cl(5.9)} + (G - W_{Ti} - W_{Ca} - W_{cl})M_{fi(5.9)}}{G}$$

$$XE_{Ti} = \frac{K_{Ti}W_{Ti}(1 + \alpha W_{cl})}{G(E_{tr}M_{5.9} + E_{fl}M_{4.5})}\{1 - \exp[-(E_{tr}M_{5.9} + E_{fl}M_{4.5})G]\} + OF_{Ti}$$

$$M_{4.5} = \frac{W_{Ti}M_{Ti(4.5)} + W_{Ca}M_{Ca(4.5)} + W_{cl}M_{cl(4.5)} + (G - W_{Ti} - W_{Ca} - W_{cl})M_{fi(4.5)}}{G}$$

3.2.e.2 Calculate Ca counts XE$_{Ca}$ $$M_{5.9} = \frac{W_{Ti}M_{Ti(5.9)} + W_{Ca}M_{Ca(5.9)} + W_{cl}M_{cl(5.9)} + (G - W_{Ti} - W_{Ca} - W_{cl})M_{fi(5.9)}}{G}$$

$$XE_{Ca} = \frac{K_{Ca}W_{Ca}(1 + \alpha W_{cl})}{G(E_{tr}M_{5.9} + E_{fl}M_{3.7})}\{1 - \exp[-(E_{tr}M_{5.9} + E_{fl}M_{3.7})G]\} + OF_{Ca}$$

$$M_{3.7} = \frac{W_{Ti}M_{Ti(3.7)} + W_{Ca}M_{Ca(3.7)} + W_{cl}M_{cl(3.7)} + (G - W_{Ti} - W_{Ca} - W_{cl})M_{fi(3.7)}}{G}$$

3.2.e.3 Calculate clay weight $$W_{cl} = \frac{\ln\left(\frac{aI_{0(T)}}{aI_{(T)}}\right) - W_{Ti}(M_{Ti} - M_{fi}) - W_{Ca}(M_{Ca} - M_{fi}) - GM_{fi}}{(M_{cl} - M_{fi})}.$$

The iterative algorithm start with initial values of weights: 0 for clay and 10% of basis weight for Ca and Ti, each, as set forth above. In each step of iteration, estimated counts XE corresponding to the assumed weights are calculated and weights are adjusted by a ratio of measured and estimated (offset-corrected) counts, first for Ti and later for Ca. A new clay weight is calculated on the basis of the ion chamber signal and newly adjusted Ti and Ca weights.

The iteration stops when the estimated counts are closer to the measured counts than a predetermined small number ε, for both Ti and Ca, or the number of iterative steps IT exceeds a maximum $IT_{max}$, whichever happens first. The output of this procedure consists of the weights of Ti, Ca, and clay.

Total raw counts for Ti, Ca, and Backscatter are defined as areas under the Gaussian curves best fitted to the normalized spectrum, spav. Each spectral peak is fitted with an individually adjusted Gaussian curve characterized by its width (sigma) and central channel. The position of a spectral peak is defined as a channel number Ch corresponding to the centroid of the Gaussian curve fitted into the peak.

The fitted spectrum, spfit, is obtained via an iterative process of minimization of $Fit_{err}$, which is defined as the sun of squared differences in each channel. The summation is performed over the entire spectrum of interest.

For diagnostic purposes, the quality of "fitting" is measured by $\chi^2$ statistic, which is equal to an average fitting error per channel.

It may be assumed that any hardware related distortions in the spectrum are of a linear nature and the position of the spectral lines is a linear function of the original position at the time of calibration. Therefore, a current position of a peak can be expressed as its original position at the time of calibration multiplied by channel slope $Ch_{slp}$ and shifted by a channel offset $Ch_{off}$, which describes the spectrum change since calibration. The sigma value for each peak is also scaled by the slope $Ch_{slp}$.

During the Peak Fit Routine (Block 3.3), both peak positions and heights are modified. The position search starts with the peak positions used at calibration $Ch_{cal(BS)}$, $Ch_{cal(TI)}$, and $Ch_{cal(Ca)}$ modified by slope and offset from the last "standardization".

The graph of FIG. 6 shows the raw spectrum (SP), an initial fit and the final best fit to the spectrum.

During the standardization routine (FIG. 7), the open-gap ion chamber signal is averaged over a standardization time period. If the signal is below an $I_{0min}$ limit, standardization fails and a "Source strength low" message is triggered. The Source Decay Ratio is calculated as a ratio of the ion chamber signals at standardization and at calibration. It should be noted that the signal at calibration is normalized to a current standardized temperature.

The open gap spectrum is collected and normalized at 60 s of "live" time. With the open gap, only two peaks are provided in the spectrum, which corresponds to backscatter and the fluorescence of argon in the air.

The positions of both peaks are found. If the positions are shifted by more than a $shift_{max}$ limit, a message to that effect is triggered and the standardization fails. The message indicates that the gain of the spectroscopy amplifier should be adjusted.

Channel slope $Ch_{slp(STZ)}$ and offset $Ch_{off(STZ)}$ at standardization are calculated in the event of an optional routine (see FIG. 8). These parameters describe spectrum distortion since calibration and are used in the peak fitting routine 3.3, described earlier. Normalized Ti, Ca, and BS counts and standardized spectrums, spav, and spfit, are then saved.

The open gap standardized spectrum should not have Ti or Ca peaks, as indicated above. The presence of either Ti or Ca peaks in the standardized spectrum indicates ash-containing paper dust on the windows. If the standardized counts of either Ti or Ca are not below predetermined limits, appropriate messages about window cleaning are triggered. These standardization counts are later subtracted from the count during measurement in order to correct for the presence of dust.

A backscatter (BS) peak should always be present at standardization. If the BS counts are outside of predetermined limits, the standardization fails. A count which is too high may indicate dirt on the windows, which contributes to backscatter. A count which is too low indicates a problem in the fluorescence detection system.

In order to better explain how the standardization routine addresses variations in gain of the spectroscopy amplifier, consider the following example wherein the gain was deliberately set to three significantly different values. The collected spectra for a paper sample is as shown in FIG. 9. Table 4 below shows the results of the standardization routine including spectrum slopes and offsets, as well as counts and Ti, Ca, and clay weights corresponding to the three spectra of FIG. 9.

TABLE 4

| Gain | 490 | 590 | 690 | Range |
|---|---|---|---|---|
| TiO2 Counts | 50782 | 51513 | 52044 | 1262 |
| CaCO3 Counts | 1681 | 1734 | 1731 | 54 |
| Backscatter Counts | 29068 | 29912 | 29640 | 844 |
| TiO2 gsm | 2.84 | 2.88 | 2.91 | 0.07 |
| CaCO3 gsm | 0.62 | 0.63 | 0.63 | 0.01 |
| Clay gsm | 0.46 | 0.27 | 0.16 | 0.29 |
| Stdz Channel Slope | 0.83 | 1.00 | 1.17 | |
| Channel Offset | −2.73 | −0.77 | −0.85 | |

From an analysis of FIG. 9 and Table 4, it will be noted that even large changes in gain are well compensated by the standardization routine of the present invention, and create only very small variations in calculated weight.

An additional routine finds the peak positions for backscatter and argon (block 4.2 of FIG. 7A). Backscatter and argon are always present in the standardized spectrum, spav. The search for each peak is done within a predetermined channel range. The search for each of the two peaks is done in two stages. A coarse Peak Find routine finds the peak position with an accuracy of 1.0 channel, and a Fine Peak Find routine finds the position within 0.1 channel.

In order to ensure that the multi-channel analyzer (MCA 44) is adapted for use and prepared to provide the X-ray fluorescence spectrum, the analyzer must also be calibrated.

During calibration, the spectroscopy amplifier gain is set to a predetermined standard value, $G_0$. A mid-value of approximately 500 is preferred. The signal caused by the back scattered X-rays with an open gap is then monitored and a peak position located (channel $N_1$). It is assumed that a standard channel (channel $N_0$) has previously been determined. It will be understood by one skilled in the art that channel position is linearly proportional to amplifier gain. Therefore, if the amplifier gain is adjusted to a value of $(N_0/N_1)*G_0$, and the peak position is observed again, the peak position will be found to be around the value of channel $N_0$. The actual value is recorded and compared at each standardization during operation in order to ensure that the MCA 44 remains calibrated throughout the calculation process.

It will be appreciated that, although a particular embodiment of the invention has been described and illustrated in detail, various changes and modifications may be made. The system of the present invention can be used with another radioisotope or X-ray tube source to measure components containing elements with higher fluorescent energies. For example, measurement of galvanized sheet metal is possible using an 241 Am radioactive source. All such changes and modifications are believed to be within the sphere and scope of the invention as defined by the claims appended hereto.

APPENDIX A

| Name as in flow charts | Description |
|---|---|
| T | Filtered air gap temperature at standardize, averaged over standardized time |
| $T_x$ | Filtered air gap temperature at measurement |
| I or $I_{(TX)}$ | Instantaneous ion-chamber reading |
| $I_{(T)}$ | Instantaneous ion-chamber reading temperature corrected to standardized temperature T |
| $I_o$ | Instantaneous ion chamber reading at standardization. |
| $_aI_{(T)}$ | Instantaneous ion-chamber reading temperature corrected to standardized temperature T, averaged over n scans (same n scans the MCA accumulate data) |
| G | Basis weight from BWM in customer units |
| n | Number of scans over which the averaging is done |
| $_aG$ | Basis weight averaged over n scans (same n scans the MCA accumulate data) |
| $t_1$ | Live integration time of MCA data accumulation |
| $spav_r$ | Raw spectrum from MCA averaged over n scans (of live time $t_1$) |
| spay | Spectrum from MCA averaged over n scans (of live time $t_1$), normalized to 60 sec. This is a vector. |
| spfit | Calculated best fit to spay (combination of Gaussians fitted to each peak). This is a vector. |
| $C_{Ti}$ | Total counts in the Titanium peak (Area under the Gaussian) |
| $C_{ca}$ | Total counts in the Calcium peak (Area under the Gaussian) |
| $C_{BS}$ | Total counts in the back scatter peak (Area under the Gaussian) |
| $X_{ti(T)}$ | Total counts in the Titanium peak normalized to original source activity and standardized temperature |
| $X_{ca(T)}$ | Total counts in the Calcium peak normalized to original source activity and standardized temperature |
| $X_{ti(o)}$ | Total counts in the Titanium peak normalized to original source activity |
| $X_{ca(O)}$ | Total counts in the Calcium peak normalized to original source activity |
| $M_{Ti}$ or $M_{Ti(5.9)}$ | Mass absorption coefficient of Titanium Dioxide for 5.9 keV X-rays in customer units |
| $M_{Ca}$ or $M_{Ca(5.9)}$ | Mass absorption coefficient of Calcium Carbonate for 5.9 keV X-rays in customer units |
| $M_{Cl}$ or $M_{Cl(5.9)}$ | Mass absorption coefficient of clay for 5.9 keV X-rays in customer units |
| $M_{fi}$ or $M_{fi(5.9)}$ | Mass absorption coefficient of fibre for 5.9 keV X-rays in customer units |
| $M_{Ti(4.5)}$ | Mass absorption coefficient of $TiO_2$ for 4.5 keV X-rays (Ti fluorescence) in customer units |
| $M_{Ca(4.5)}$ | Mass absorption coefficient of $CaCO_3$ for 4.5 keV X-rays (Ti fluorescence) in customer units |
| $M_{cl(4.5)}$ | Mass absorption coefficient of clay for 4.5 keV X-rays (Ti fluorescence) in customer units |
| $M_{fi(4.5)}$ | Mass absorption coefficient of fibre for 4.5 keV X-rays (Ti fluorescence) in customer units |
| $M_{Ti(3.7)}$ | Mass absorption coefficient of $TiO_2$ for 3.7 keV X-rays (Ti fluorescence) in customer units |
| $M_{Ca(3.7)}$ | Mass absorption coefficient of $CaCO_3$ for 3.7 keV X-rays (Ti fluorescence) in customer units |
| $M_{cl(3.7)}$ | Mass absorption coefficient of clay for 3.7 keV X-rays (Ti fluorescence) in customer units |
| $M_{fi(3.7)}$ | Mass absorption coefficient of fibre for 3.7 keV X-rays (Ti fluorescence) in customer units |
| $M_{5.9}$ | Total mass absorption coefficient of paper for 5.9 keV X-rays |
| $M_{4.5}$ | Total mass absorption coefficient of paper for 4.5 keV X-rays |
| $M_{3.7}$ | Total mass absorption coefficient of paper for 3.7 keV X-rays |
| $M_A$ | Calculated mass absorption coefficient of total ash after determining ash components |
| $K_{ti}$ | Slope required to fit calculated Ti counts to actual counts at calibration |
| $K_{ca}$ | Slope required to fit calculated Ca counts to actual counts at calibration |

APPENDIX A-continued

| Name as in flow charts | Description |
|---|---|
| $OF_{Ti}$ | Offset required to fit calculated Ti counts to actual counts at calibration |
| $OF_{ca}$ | Offset required to fit calculated Ca counts to actual counts at calibration |
| $E_{tr}$ | Geometrical factor for source emitted X-rays (5.9 keV) |
| $E_{fi}$ | Geometrical factor for fluorescent X-rays (4.5 and 3.7 keV) |
| $W_{ti}$ | Calculated $TiO_2$ weight per unit area (in customer units) |
| $W_{ca}$ | Calculated $CaCO_3$ weight per unit area (in customer units) |
| $W_{cl}$ | Calculated clay weight per unit area (in customer units) |
| $XE_{Ti}$ | Estimated counts for $TiO_2$ in the iterative calculation |
| $XE_{Ca}$ | Estimated counts for $CaCO_3$ in the iterative calculation |
| $XE_{cl}$ | Estimated counts for clay in the iterative calculation |
| IT | Iteration count |
| $IT_{max}$ | Maximum number of iterations allowed |
| $\epsilon$ | Maximum error allowed in iterative refinement |
| $A\%_{Ti}$ | Calculated Ti ash percentage |
| $A\%_{Ca}$ | Calculated Ca ash percentage |
| $A\%_{cl}$ | Calculated clay ash percentage |
| $A\%$ | Calculated total ash percentage |
| $Ch_{Off}$ | Channel offset for MCA spectrum |
| $Ch_{Off(stz)}$ | Channel offset for MCA spectrum at standardize |
| $Ch_{slp}$ | Channel slope for MCA spectrum |
| $Ch_{slp(stz)}$ | Channel slope for MCA spectrum at standardization |
| $Fit_{err}$ | Current fit error |
| $Ch_{cal(BS)}$ | Channel position of the backscatter peak maximum at calibration |
| $Ch_{cal(Ti)}$ | Channel position of the Ti peak maximum at calibration |
| $Ch_{cal(Ca)}$ | Channel position of the Ca peak maximum at calibration |
| $x^2$ | Calculated quality of fitting |
| $Ch_{first}$ | First channel of the MCA spectrum |
| $Ch_{last}$ | Last channel of the MCA spectrum |
| $I_{OL(Tc)}$ | Open gap ion chamber reading at installation |
| $I_{OL(T)}$ | Open gap ion chamber reading at installation, normalized to current standardized temperature |
| $T_c$ | Temperature when 'OL(Tc)' was recorded at installation |
| $S_{RD}$ | Source decay ratio |
| $_aI_O$ or $_aI_{O(T)}$ | Open gap ion chamber reading averaged over standardization time |
| $I_{Omin}$ | Minimum open gap ion chamber reading allowed (alarm limit) |
| $Ch_{stz(bs)}$ | Channel position of the backscatter peak maximum found at standardization |
| $Ch_{stz(Ar)}$ | Channel position of the Argon peak maximum found at standardization |
| $Ch_{cal(Ar)}$ | Channel position of the Argon peak maximum found at calibration |
| $Shift_{max}$ | Maximum MCA channel shift allowed since calibration (alarm limit) |
| $spav_{stz}$ | Spectrum from MCA averaged over n scans (of live time $t_L$), normalized to 60 sec. At standardize. This is a vector. |
| $spfit_{stz}$ | Calculated best fit to spay (combination of Gaussians fitted to each peak) at standardize. This is a vector. |
| $X_{ti(stz)}$ | Total counts in the Titanium peak normalized to original source activity at standardization (due to window contamination) |
| $X_{Ca(stz)}$ | Total counts in the Calcium peak normalized to original source activity at standardization (due to window contamination) |
| $X_{BS(Stz)}$ | Total counts in the backscatter peak normalized to original source activity at standardization (due to window) |
| $X_{ti(stz)max}$ | Maximum total counts allowed in the Titanium peak normalized to original source activity at standardization (due to window contamination). (warning limit) |
| $X_{Ca(stz)max}$ | Maximum total counts allowed in the Calcium peak normalized to original source activity at standardization (due to window contamination). (warning limit) |
| $X_{BS(stz)max}$ | Maximum total counts allowed in the backscatter peak normalized to original source activity at standardization (due to window dust). (alarm limit) |
| $X_{BS(stz)min}$ | Minimum total counts allowed in the backscatter peak normalized to original source activity at standardization (check for Si detector deterioration). (alarm limit) |

APPENDIX A-continued

| Name as in flow charts | Description |
|---|---|
| $ChC_{stz(bs)}$ | Coarse channel position of the backscatter peak maximum found at standardization |
| $ChC_{stz(Ar)}$ | Coarse channel position of the Argon peak maximum found at standardization |
| $Ch_{mean}$ | Current value of $Ch_{stz}$ within the fine peak find routine at standardization |

What is claimed is:

1. A system for measuring composition of components in a sheet material containing a plurality of additives, comprising:
   a radiation source for irradiating said sheet material;
   a first detector located on a side of said sheet material opposite said radiation source for measuring radiation passing through said sheet material and in response generating a first intensity signal related to content of said components in said sheet material;
   a second solid state detector located on a side of said sheet material adjacent said radiation source for measuring fluorescence radiation from said sheet material to provide a normalized spectrum having a plurality of peaks representing respective ones of said additives and in response generating a plurality of count values representing areas under said respective peaks;
   means for providing basis weight of said sheet material; and
   computing means for (i) calculating respective individual weights of said plurality of additives from said plurality of count values, said first intensity signal, and said basis weight, (ii) calculating an average mass absorption coefficient of the sheet material based on said respective individual weights of said additives, said first intensity signal, and said basis weight, (iii) calculating total weight of said components based on said absorption coefficient, said first intensity signal and said basis weight, and (iv) converting to and outputting total and individual percentages of said components based on ratios of said total weight and said individual weights to said basis weight.

2. The system of claim 1, wherein said radiation source generates X-rays and said second detector further comprises a solid state X-ray detector and multi-channel analyzer for generating a raw spectrum based on a plurality of traverses of said first detector past said sheet material, means for averaging said raw spectrum to create said normalized spectrum, and means for fitting curves to said respective peaks and calculating said plurality of count values.

3. The system of claim 2, wherein said solid state X-ray detector further comprises a silicon-PIN photodiode, a source of high bias voltage applied across said detector for collecting electric charge generated as a result of interaction between said fluorescence radiation and said photodiode, and means for cooling said fluorescence detector.

4. The system of claim 3, wherein said means for cooling comprises two levels of thermoelectric cooling devices surrounding said silicon-PIN photodiode.

5. The system of claim 1, wherein said sheet material is paper and said components consist of titanium dioxide, calcium carbonate, and clay.

6. The system of claim 1, wherein said means for providing basis weight of said sheet material comprises a basis weight gauge for measuring mass per unit area of said sheet material and generating a value representative thereof.

7. The system of claim 1, wherein said means for providing basis weight of said sheet material comprises a register for storing a pre-set value of mass per unit area of said sheet material.

8. A method of measuring composition of inorganic material in a sheet material containing a plurality of additives, comprising the steps of:
   scanning said sheet material past a source of radiation;
   measuring radiation passing through said sheet material and in response generating a first intensity signal related to content of said inorganic material in said sheet material;
   measuring fluorescence radiation from said sheet material to provide a normalized spectrum having a plurality of peaks representing respective ones of said additives;
   generating a plurality of count values representing areas under a plurality of said respective peaks representing respective ones of said additives;
   obtaining basis weight of said sheet material;
   calculating respective individual weights of said plurality of additives from said plurality of count values, said first intensity signal, and said basis weight;
   calculating an average mass absorption coefficient of the sheet material based on said respective individual weights of said additives, said first intensity signal, and said basis weight;
   calculating total weight of said inorganic material based on said absorption coefficient, said first intensity signal and said basis weight; and
   converting to and outputting total and individual percentages of said inorganic material and individual additives based on ratios of said total weight and said individual weights to said basis weight.

9. The method of claim 8, further comprising the steps of:
   measuring open gap fluorescence radiation of argon in air and back scatter without said sheet material to provide a further normalized spectrum having a pair of peaks representing respective ones of said back scatter and said fluorescence of argon in air at standardization;
   locating said pair of peaks in terms of respective channel numbers corresponding to the centroids of a pair of curves fitted into said pair of peaks;
   calculating channel slope and channel offset from said respective channel numbers at standardization for defining spectrum distortion; and
   applying said channel slope and channel offset to said step of generating said plurality of count values representing respective ones of said additives.

10. The method of claim 9, further comprising the steps of generating a warning of excessive dust collection in the event said further normalized spectrum contains more than said pair of peaks, and a response further correcting said plurality of count values.

11. The method of claim 8, further comprising the steps of:
   receiving an instantaneous value of said total percentage of inorganic material;
   receiving an instantaneous position value of said sheet material prior to said step of scanning; and
   generating a cross-directional profile of said instantaneous value of said total percentage of inorganic material relative to said instantaneous position value of said sheet material past said source of radiation.

12. The method of claim 8, wherein said step of calculating respective individual weights of said plurality of additives further comprises multiplying said count values by a predetermined calibration parameter related to clay or talc weight in said sheet material for empirical correction of mutual interaction between the fluorescence radiation generated by additives of higher atomic number and clay or talc.

* * * * *

UNITED STATES PATENT AND TRADEMARK OFFICE
CERTIFICATE OF CORRECTION

PATENT NO. : 6,421,415 B1
DATED : July 16, 2002
INVENTOR(S) : Marek Peczkis et al.

It is certified that error appears in the above-identified patent and that said Letters Patent is hereby corrected as shown below:

<u>Column 9,</u>
Table 2, line 63, after "accumulated", add -- average (refer to flow chart) --.

Signed and Sealed this

Twelfth Day of November, 2002

Attest:

Attesting Officer

JAMES E. ROGAN
*Director of the United States Patent and Trademark Office*